(12) United States Patent
Galindo Sevilla et al.

(10) Patent No.: US 8,664,384 B2
(45) Date of Patent: Mar. 4, 2014

(54) N⁶-(FERROCENMETHYL)QUINAZOLIN-2,4,6-TRIAMINA (H2) AND THE DERIVATIVES AND PRODRUGS THEREOF AS ANTILEISHMANIAL, ANTIPROTOZOAL, ANTIPARASITIC AND ANTIMICROBIAL AGENTS

(75) Inventors: Norma del Carmen Galindo Sevilla, Huixquilucan (MX); Francisco Hernández Luis, Huixquilucan (MX)

(73) Assignee: Norma del Carmen Galindo Sevilla, Huixquilucan (MX)

( * ) Notice: Subject to any disclaimer, the term of this patent is extended or adjusted under 35 U.S.C. 154(b) by 0 days.

(21) Appl. No.: 13/643,949

(22) PCT Filed: Feb. 21, 2011

(86) PCT No.: PCT/MX2011/000025
§ 371 (c)(1),
(2), (4) Date: Jan. 15, 2013

(87) PCT Pub. No.: WO2011/136631
PCT Pub. Date: Nov. 3, 2011

(65) Prior Publication Data
US 2013/0109663 A1    May 2, 2013

(30) Foreign Application Priority Data
Mar. 16, 2010   (MX) .................... MX/a/2010/002868

(51) Int. Cl.
*C07F 17/02*   (2006.01)

(52) U.S. Cl.
USPC .......................................... 544/225; 514/187

(58) Field of Classification Search
None
See application file for complete search history.

(56) References Cited

PUBLICATIONS

Howarth et al. in Bioorganic and Medicinal Chemistry Letters 13 (2003) 2017-2020.*

* cited by examiner

*Primary Examiner* — Dennis Heyer
(74) *Attorney, Agent, or Firm* — Sam K. Tahmassebi; TechLaw LLP (57) ABSTRACT

The use of N⁶-(ferrocenmethyl)quinazoline-2,4,6-triamine (H2), its derivatives, and prodrugs that present antimicrobial (antibiotic, microbicide), antiparasitic (parasiticide), antiprotozoal (protozoacide), and antileishmanial (leishmanicide) activities, as well as its use as a drug in vertebrates (humans and animals).

13 Claims, 5 Drawing Sheets

N6-(FERROCENMETHYL)QUINAZOLIN-2,4,6-TRIAMINA (H2) AND THE DERIVATIVES AND PRODRUGS THEREOF AS ANTILEISHMANIAL, ANTIPROTOZOAL, ANTIPARASITIC AND ANTIMICROBIAL AGENTS

RELATED APPLICATIONS

The present application is filed under 35 U.S.C. §371 as the U.S. national phase of International Application PCT/MX2011/000025, filed Feb. 21, 2011, which designated the U.S. and claims priority to the Mexican Application Serial No. MX/a/2010/002868, filed on Apr. 26, 2010, by Norma del Carmen Galindo Sevilla et al., the entire disclosure of both of which is incorporated herein by reference.

BACKGROUND

The use of $N^6$-(ferrocenmethyl)quinazoline-2,4,6-triamine as an antimicrobial, antibiotic, microbicide, bacteriological, bacteriostatic, antiparasitic, antiprotozoal, or antileishmanial agent has not been previously reported.

Since the emergence of leishmaniasis in 1885, few agents have been described and used in the treatment of this disease, and these agents have variable efficiency and effectiveness. Therapeutic options are rare and include expensive drugs that are difficult to obtain, lack a coordinated registry, and may be toxic or ineffective. Antimonials, for example (including the meglumine antimoniate), were introduced in 1940 and continue to be the treatment of choice for cutaneous leishmaniasis, although the treatment regimens are longer than 20 days and can induce pancreatitis (the most frequent reason that treatment is discontinued) as well as serious electrocardiographic changes. Amphotericin B, which is nephrotoxic and hypercalcemic, is also used (Alvar J, et al., 1997. *Clin. Microbiol. Rev.* 10: 298-319; Alvar J, et al., 2008. *Clin. Microbiol. Rev.* 21: 334-359).

Other compounds used as antiparasites, such as metronidazole, present variable results, which in general reflects a lack of evidence regarding these drugs. Recently, the in vitro leishmanicidal activity of hydroxyurea was described (Martinez-Rojano H, et al., 2008. *Antimicrob. Agents Chemother.* 52: 3642-3647), although in vivo evidence has not been reported.

THE SUBJECT MATTER OF THE INVENTION

The present invention refers to the human or veterinary use of a compound that contains $N^6$-(ferrocenmethyl)quinazoline-2,4,6-triamine, as well as its derivatives and prodrugs, as an antimicrobial (antibiotic, microbicide), antiparasitic (parasiticide), antiprotozoal (protozoacide), or antileishmanial (leishmanicide) agent.

The $N^6$-(ferrocenmethyl)quinazoline-2,4,6-triamine compound, which we refer to as H2, presents antimicrobial, antiparasitic, and leishmanicide activity from 0.1 μg/ml to greater than 100 μg/ml. H2 can be used in the treatment of infections caused by microorganisms, parasites, and protozoa, including members of the *Leishmania* genus in particular.

DESCRIPTION OF THE INVENTION

Description of the Compound

Figure 1:
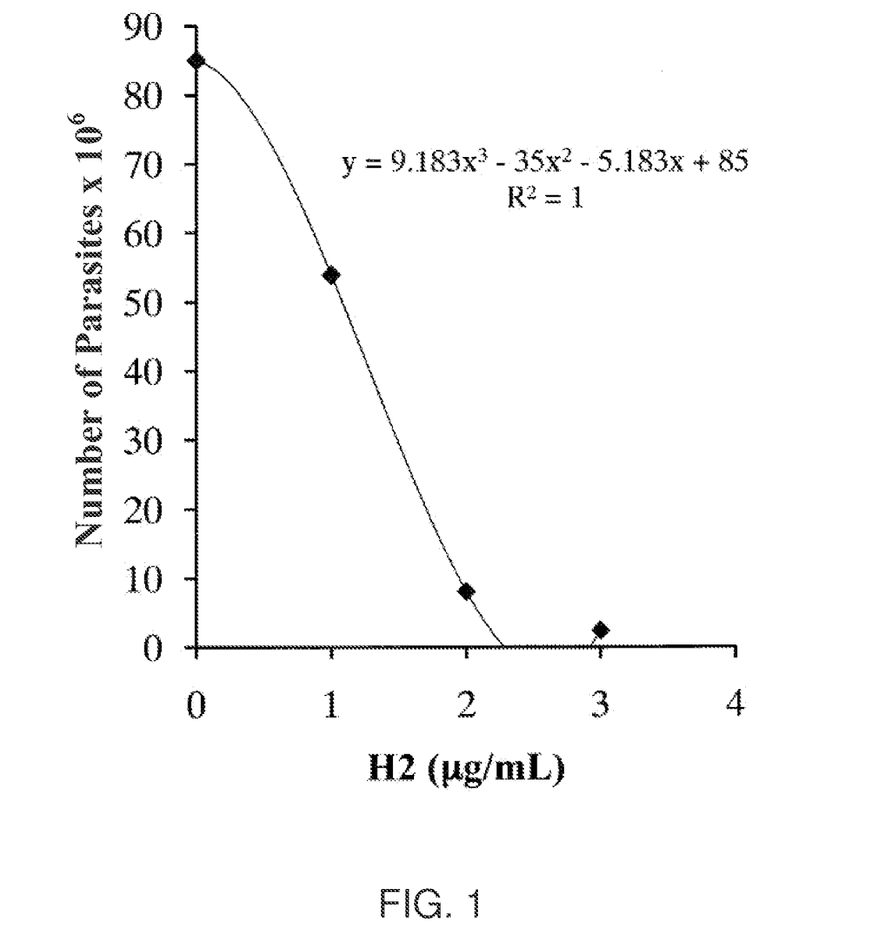
FIG. 1: The biological activity of H2 toward the in vitro growth of *Leishmania mexicana* strain MHOM/MX/01/Tab3. A growth curve collected after 72 hours of parasite cultivation in a Neubauer chamber in the presence of the H2 is shown. The H2 concentration is shown on the horizontal axis, whereas the number of parasites/ml is shown on the vertical axis. The experiment was performed at room temperature using high-glucose Dulbecco's Modified Eagle's Medium with 10% fetal bovine serum.
Figure 2:
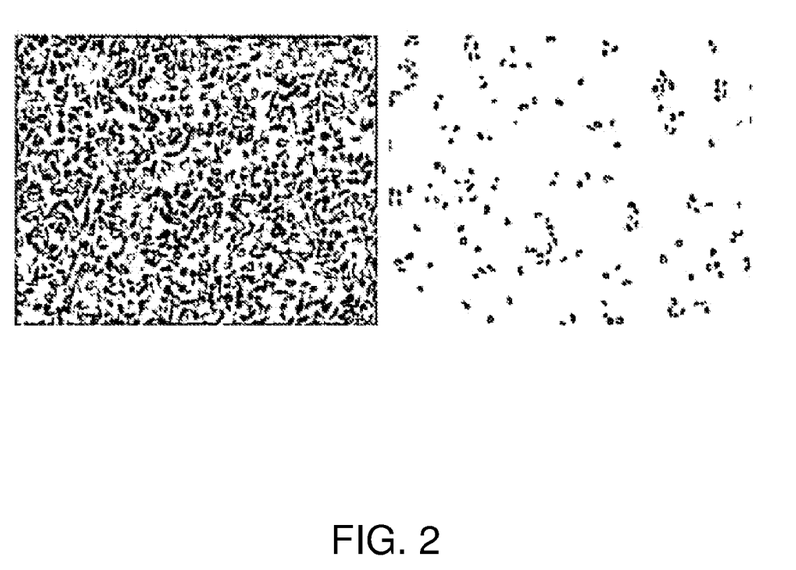
FIG. 2: Photograph obtained using an inverted microscope showing the inhibition of *Leishmania* growth by H2. The parasite culture shown in the left image was grown under the same conditions described in FIG. 1 but with the absence of H2. The right image shows a culture grown in the presence of 1 μg/ml of the H2 compound, indicating a clear lack of growth and destruction of the parasite in the presence of H2.
Figure 3:
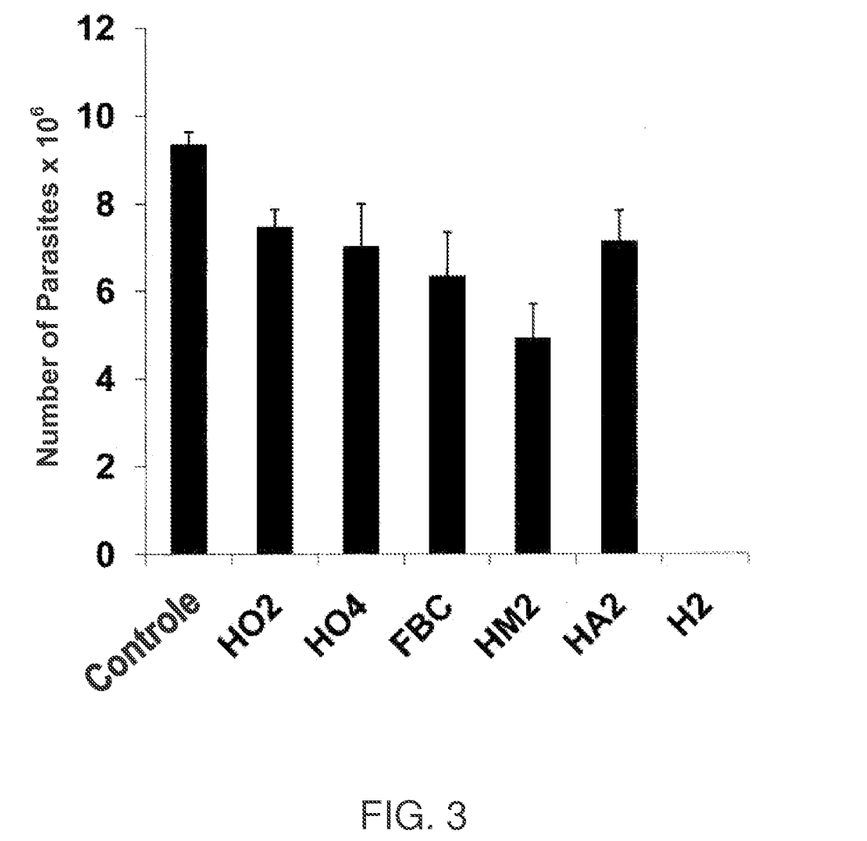
FIG. 3: A plot showing the H2 prodrug activity toward the in vitro growth of *Leishmania Mexicana*. To obtain a higher sensitivity in this experiment, the MNYC/BZ/62/M379 reference strain, which has a higher sensitivity to H2 than does MHOM/MX/01/Tab3, was used. The number of parasites/ml was determined at 72 hours of incubation using 100 mM of each compound in four replicates. The culture conditions were the same as described in FIG. 1.
Figure 4:
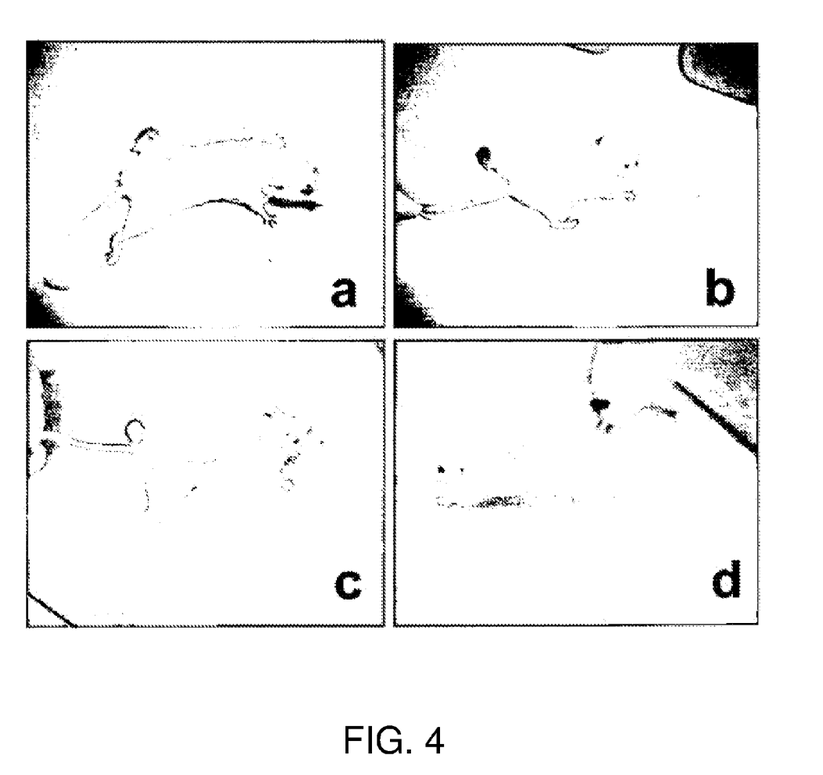
FIG. 4: An example of biological activity of H2 parenterally administered at a dose of 0.1 mg/mL in 100 μl of physiological saline solution; a) and c) correspond to the activity prior to treatment, b) is a control using only a saline solution, and d) is the condition with H2. Images b) and d) were collected at 14 days after treatment.
Figure 5:
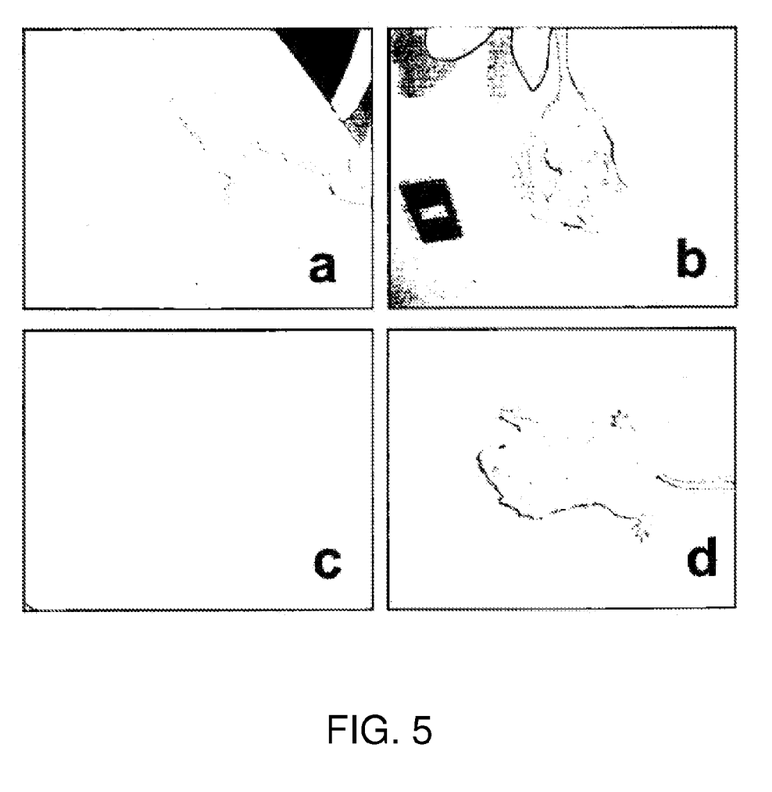
FIG. 5: An example of the biological activity of the HA2 prodrug dissolved in drinking water and orally administered at a dose of 1 mg/mL ad libitum for 3 days; a) before treatment, b) three months after treatment, c) six months after treatment, and d) seven months after treatment.

The compound $N^6$-(ferrocenmethyl)quinazoline-2,4,6-triamine (H2) is a solid substance at room temperature and atmospheric pressure. Its contains carbon, hydrogen, nitrogen and iron (II) and has a molecular weight of 374 a.m.u., a condensed molecular formula $C_{19}H_{19}N_5Fe$, and the following chemical structure:

H2 presents the following physicochemical properties:
Melting point: 210.6-211° C.
$R_f$: 0.53 (2-butanol/acetic acid/water 80:20:5)
Infrared spectrum (KBr): 3369 and 3244 (N—H), 1693 and 1668 (C=O), 823 (C—H ferrocene).

Proton nuclear magnetic resonance spectrum (DMSO-$d_6$): 3.98 ppm (t, J=6, 2H, $CH_2$), 4.10 ppm (t, J=3, 2H, ferrocene), 4.20 ppm (s, 5H, ferrocene), 4.32 ppm (t, J=3, 2H, ferrocene), 5.3 ppm (t, J=6, 2H, $CH_2$), 5.51 ppm (s, 2H, $NH_2$), 6.96 ppm (d, J=2.4, 1H, quinazoline), 7.02 ppm (s, 1H, $NH_2$), 7.04 ppm (br., s, 1H, quinazoline), 7.049 ppm (br, s, 1H, quinazoline).

Elemental analysis for $C_{19}H_{20}FeN_5$: Calculated: C, 61.14; H, 5.13; N, 18.76. Measured: C, 61.14; H, 4.92; N, 18.03.

H2 synthesis is initiated by the condensation of N,N'-(6-aminoquinazoline-2,4-diyl)diacetamide with ferrocencarboxaldehyde in dimethylformamide (DMF). Subsequent reduction with sodium borohydride ($NaBH_4$) gives HA2, which produces H2 in a 62% yield when hydrolyzed in a methanolic sodium hydroxide solution.

N,N-(6-aminoquinazoline-2,4-diyl) diacetamide ferrocencarboxaldehyde

HA2

H2

It is also possible to prepare H2 prodrugs, i.e., compounds with the same base structure that form H2 when metabolized in a living organism.

TABLE

H2 Prodrugs

| No. | $R_1$ | $R_2$ | $R_3$ |
| --- | --- | --- | --- |
| HA2 | $NHC(O)CH_3$ | $NHC(O)CH_3$ | H |
| 2 | $NHCOCH_2CH_2COOH$ | $NH_2$ | H |
| 3 | $NH_2$ | $NHCOCH_2CH_2COOH$ | H |
| 4 | $NHCOCH_2CH_2COOH$ | $NHCOCH_2CH_2COOH$ | H |
| 5 | $NHCOCH_2CH_2COONHC(NH)NH_2$ | $NH_2$ | H |
| 6 | $NH_2$ | $NHCOCH_2CH_2COONHC(NH)NH_2$ | H |
| 7 | $NHCOCH_2CH_2COONHC(NH)NH_2$ | $NHCOCH_2CH_2COONHC(NH)NH_2$ | H |

These compounds can be obtained using the following process:

The synthesis of prodrugs 2 and 3 is initiated by reacting one equivalent of succinic anhydride with H2 in DMF. After stirring at room temperature until the reactants are consumed, the resulting suspension is separated by filtration. The mixture of the obtained compounds (2 and 3) is separated by open column chromatography using silica gel as the stationary phase and chloroform as the mobile phase. The synthesis of prodrugs 4 and 7 is initiated by reacting two equivalents of succinic anhydride with H2 in DMF. After stirring at room temperature until the reactants are consumed, the suspended solution is separated by filtration to obtain prodrug 4, which is reacted with dicyclohexylcarbodiimide and hydroxyurea in DMF at room temperature for 72 hours. The reaction mixture is separated by open column chromatography using silica gel as the stationary phase and a chloroform/methanol gradient as the mobile phase to obtain prodrug 7.

Pharmaceutical Composition:

As part of the invention, the pharmaceutical compositions of H2, derivatives and prodrugs are also presented along with the pharmaceutically acceptable excipients. The following excipients can be employed for the compound synthesis: low-molecular-weight carboxymethylcellulose, high-molecular-weight carboxymethylcellulose, ethanol, Tween 20, Tween 80, Cremophor, polyethylene glycol, propylene glycol, glycerol, triethanolamine, lactose, alpha-cyclodextrin, beta-cyclodextrin, hydroxypropyl-beta-cyclodextrin, heptakis, methyl-beta-cyclodextrin, and gamma-cyclodextrin.

Administration Routes:

The administration of H2, derivatives or prodrugs to biological organisms is performed by any pharmaceutical route that is used and accepted for that purpose.

Biological Activity:

At greater than 5 µg/ml, H2 is lethal to *Leishmania* in less than 5 hours. The in vitro effect is apparent at 30 minutes after application. The parasite structure is modified such that it loses its characteristic form, loses refringence, becomes spherical, and is incapable of multiplying. H2 has a $CL_{50}$ of 2.6 µm/ml for the *Leishmania mexicana* MHOM/MX/01/Tab3 strain. The mechanism of cellular damage could not be identified by means of annexin for concentrations greater than 10 µg/ml; it is thought that a necrosis process rather than apoptosis is likely involved.

In comparison to other compounds with leishmanicidal activity, such as meglumine antimoniate, metronidazole, or hydroxyurea, H2 kills the total amount of parasites more quickly at up to 10-fold faster than any previously described compounds at doses that are ten-fold lower or less. H2 also presents activity against other protozoa, including *Trypanosoma*, *Plasmodium*, *Entamoeba*, and *Giardia*, as well as metazoan parasites and microorganisms in general.

Cytotoxicity against murine cells was not found in in vitro studies or in vivo studies using oral, parenteral, or dermal administration in mice. The compound was designed to specifically inhibit the activity of vital protozoan enzymes without activity in the human versions.

EXAMPLES

1) Synthesis

Using a 50 ml Florence flask equipped with magnetic stirring, a Vigreux column, and a nitrogen atmosphere, 0.31 g of ferrocencarboxaldehyde (0.00143), 0.3 g of N,N'-(6-aminoquinazoline-2,4-diyl)diacetamide (1 eq.), 1 ml of DMF, and a drop of acetic acid were combined. The mixture was stirred at 85° C. for 45 minutes. The mixture was cooled to 0° C. using an ice-water bath, and 0.0671 g (2 eq.) of $NaBH_4$ was slowly added. The ice bath was removed, and stirring was continued for 12 hours at room temperature. The DMF was evaporated in a rotatory evaporator, and a saturated solution of $Na_2CO_3$ was added to the residue. The yellow precipitate that formed was separated by filtration and rinsed several times with water. After drying at room temperature, the solid was rinsed several times with diisopropyl ether to obtain 0.3239 g of HA2 with a 48% yield, $R_f$=0.76 ($CHCl_3$/MeOH 80:20) and p.f.=218-220° C. HA2 was hydrolyzed with one equivalent of a methanolic sodium hydroxide solution to obtain a precipitate that was separated by filtration. The solid was cleaned in methanol with activated carbon. From this procedure, 0.32 g of a yellow compound (H2) was obtained at a 62% yield, $R_f$=0.53 (2-butanol/acetic acid/water 80:20:5) and p.f.=210.6-211° C.

2) Biological Activity

H2 (3 µg/ml) eliminates more than 90% of the parasites in *Leishmania mexicana* cultures (Tab3 or M379 strain) with $10^6$ parasites/ml in Dulbecco's medium modified with 4.5 mg/mL glucose and 10% fetal bovine serum.

3) Pharmaceutical Preparation

To prepare a suspension of H2, 10 mg of the substance was dissolved in 1 ml of DMF. Subsequently, 100 µl of the solution was diluted with water (1:10) to obtain a suspension for oral administration to rodents.

4) H2 Derivatives

| No. | $R_1$ | $R_2$ | $R_3$ |
| --- | --- | --- | --- |
| 8 | $NHC(O)CH_3$ | $NHC(O)CH_3$ | $CH_3$ |
| 9 | $NHCOCH_2CH_2COOH$ | $NH_2$ | $CH_3$ |
| 10 | $NH_2$ | $NHCOCH_2CH_2COOH$ | $CH_3$ |
| 11 | $NHCOCH_2CH_2COOH$ | $NHCOCH_2CH_2COOH$ | $CH_3$ |
| 12 | $NHCOCH_2CH_2COONHC(NH)NH_2$ | $NH_2$ | $CH_3$ |
| 13 | $NH_2$ | $NHCOCH_2CH_2COONHC(NH)NH_2$ | $CH_3$ |
| 14 | $NHCOCH_2CH_2COONHC(NH)NH_2$ | $NHCOCH_2CH_2COONHC(NH)NH_2$ | $CH_3$ |
| 15 | $NHC(O)CH_3$ | $NHC(O)CH_3$ | $CH_3CH_2$ |
| 16 | $NHCOCH_2CH_2COOH$ | $NH_2$ | $CH_3CH_2$ |
| 17 | $NH_2$ | $NHCOCH_2CH_2COOH$ | $CH_3CH_2$ |
| 18 | $NHCOCH_2CH_2COOH$ | $NHCOCH_2CH_2COOH$ | $CH_3CH_2$ |
| 19 | $NHCOCH_2CH_2COONHC(NH)NH_2$ | $NH_2$ | $CH_3CH_2$ |
| 20 | $NH_2$ | $NHCOCH_2CH_2COONHC(NH)NH_2$ | $CH_3CH_2$ |
| 21 | $NHCOCH_2CH_2COONHC(NH)NH_2$ | $NHCOCH_2CH_2COONHC(NH)NH_2$ | $CH_3CH_2$ |

-continued

| No. | R₁ | R₂ | R₃ |
|---|---|---|---|
| HO2 | $NH_2$ | OH | H |
| HO4 | OH | $NH_2$ | H |
| HO24 | OH | OH | H |

5) Prodrug Synthesis

In a 50 ml Florence flask equipped with magnetic stiffing, a Vigreux column, and a nitrogen atmosphere, 0.31 g of ferrocencarboxaldehyde (0.00143), 0.3 g of N,N'-(6-aminoquinazoline-2,4-diyl)diacetamide (1 eq.), 1 ml of DMF, and a drop of acetic acid were combined. The mixture was stirred at 85° C. for 45 minutes. The mixture was cooled to 0° C. in an ice-water bath, and 0.0671 g (2 eq.) of $NaBH_4$ was slowly added. The ice bath was removed, and stirring was continued for 12 hours at room temperature. Subsequently, the DMF was evaporated in a rotary evaporator. A saturated solution of $Na_2CO_3$ was added to the residue. The yellow precipitate that formed was separated by filtration and rinsed several times with water. After drying at room temperature, the solid was rinsed several times with diisopropyl ether to obtain 0.3239 g of HA2 at 48% yield, $R_f$=0.76 ($CHCl_3$/MeOH 80:20) and p.f.=218-220° C.

6) Biological Activity of the HA2 Prodrug and the Derivatives HO2 and HO4

The following is a list of *Leishmania mexicana* growth inhibition activity by the prodrugs compared to H2 and a control.

| Compound | % of *Leishmania* Growth Inhibition |
|---|---|
| Control | 0 |
| HO2 | 20 |
| HO4 | 25 |
| FBC | 32 |
| HA2 | 24 |
| H2 | 100 |

FBC: N-(ferrocenmethyl)aniline

The invention claimed is:

1. A compound selected from the group consisting of H2, HA2, 2-21, HO2, HO4, and HO24, wherein the compound has the structure of Formula (1), and wherein $R_1$, $R_2$, and $R_3$ are as set forth in the table below:

Formula (1)

| No. | R₁ |
|---|---|
| H2 | $NH_2$ |
| HA2 | $NHC(O)CH_3$ |
| 2 | $NHCOCH_2CH_2COOH$ |
| 3 | $NH_2$ |
| 4 | $NHCOCH_2CH_2COOH$ |
| 5 | $NHCOCH_2CH_2COONHC(NH)NH_2$ |
| 6 | $NH_2$ |
| 7 | $NHCOCH_2CH_2COONHC(NH)NH_2$ |
| 8 | $NHC(O)CH_3$ |
| 9 | $NHCOCH_2CH_2COOH$ |
| 10 | $NH_2$ |
| 11 | $NHCOCH_2CH_2COOH$ |
| 12 | $NHCOCH_2CH_2COONHC(NH)NH_2$ |
| 13 | $NH_2$ |
| 14 | $NHCOCH_2CH_2COONHC(NH)NH_2$ |
| 15 | $NHC(O)CH_3$ |
| 16 | $NHCOCH_2CH_2COOH$ |
| 17 | $NH_2$ |
| 18 | $NHCOCH_2CH_2COOH$ |
| 19 | $NHCOCH_2CH_2COONHC(NH)NH_2$ |
| 20 | $NH_2$ |
| 21 | $NHCOCH_2CH_2COONHC(NH)NH_2$ |
| HO2 | $NH_2$ |
| HO4 | OH |
| HO24 | OH |

| No. | R₂ | R₃ |
|---|---|---|
| H2 | $NH_2$ | H |
| HA2 | $NHC(O)CH_3$ | H |
| 2 | $NH_2$ | H |
| 3 | $NHCOCH_2CH_2COOH$ | H |
| 4 | $NHCOCH_2CH_2COOH$ | H |
| 5 | $NH_2$ | H |
| 6 | $NHCOCH_2CH_2COONHC(NH)NH_2$ | H |
| 7 | $NHCOCH_2CH_2COONHC(NH)NH_2$ | H |
| 8 | $NHC(O)CH_3$ | $CH_3$ |
| 9 | $NH_2$ | $CH_3$ |
| 10 | $NHCOCH_2CH_2COOH$ | $CH_3$ |
| 11 | $NHCOCH_2CH_2COOH$ | $CH_3$ |
| 12 | $NH_2$ | $CH_3$ |
| 13 | $NHCOCH_2CH_2COONHC(NH)NH_2$ | $CH_3$ |
| 14 | $NHCOCH_2CH_2COONHC(NH)NH_2$ | $CH_3$ |
| 15 | $NHC(O)CH_3$ | $CH_3CH_2$ |
| 16 | $NH_2$ | $CH_3CH_2$ |

-continued

Formula (1)

| 17 | NHCOCH$_2$CH$_2$COOH | CH$_3$CH$_2$ |
| 18 | NHCOCH$_2$CH$_2$COOH | CH$_3$CH$_2$ |
| 19 | NH$_2$ | CH$_3$CH$_2$ |
| 20 | NHCOCH$_2$CH$_2$COONHC(NH)NH$_2$ | CH$_3$CH$_2$ |
| 21 | NHCOCH$_2$CH$_2$COONHC(NH)NH$_2$ | CH$_3$CH$_2$ |
| HO2 | OH | H |
| HO4 | NH$_2$ | H |
| HO24 | OH | H. |

2. The compound of claim 1, wherein the compound is $N^6$-(ferrocenmethyl)quinazoline-2,4,6-triamine (H2) with the following chemical structure:

3. A pharmaceutical composition comprising a compound of claim 1, in combination with a pharmaceutically accepted excipient or adjuvant.

4. The pharmaceutical composition of claim 3, wherein the compound of claim 1 is H2.

5. The pharmaceutical composition of claim 3, wherein the composition is formulated in tablet, capsule, injectable drug, patch, suspension, gel, or granulated form.

6. The pharmaceutical composition of claim 3, wherein the compound of claim 1 is selected from the group consisting of HA2, 2-21, HO2, HO4, and HO24.

7. A process for the preparation of a compound of claim 1, the process comprising the steps of:
   i) condensing N,N'-(6-aminoquinazoline-2,4-diyl)diacetamide with ferrocencarboxaldehyde in dimethyl formamide (DMF) to obtain a condensation product; and
   ii) reducing the condensation product to obtain a reduction product; or
   i) reacting of 2,4,6-triaminquinazoline with methyl iodide or ethyl iodide to obtain an alkylated compound; and
   ii) coupling the alkylated compound with ferrocencarboxaldehyde to obtain a ferrocenmethylquinazoline compound.

8. The process of claim 7, further comprising the step of hydrolyzing the reduction product to obtain a hydrolyzed product.

9. The process of claim 8, further comprising the step of reacting the hydrolyzed product with succinic anhydride at room temperature.

10. The process of claim 9, further comprising the step of reacting the product of claim 9 with hydroxyurea using dicyclohexylcarbodiimide.

11. The process of claim 8, further comprising reacting the hydrolyzed product with sodium hydroxide.

12. A method of treating a microbial disease comprising identifying a subject in need thereof and administering to the subject a compound of claim 1, wherein the microbial disease is a *Leishmanial* disease.

13. The method of claim 12, wherein the subject is a human or an animal.

* * * * *